US00PP17131P2

(12) United States Plant Patent
Egger

(10) Patent No.: US PP17,131 P2
(45) Date of Patent: Oct. 3, 2006

(54) ***HEUCHERA* PLANT NAMED 'PEACH MELBA'**

(50) Latin Name: ***Heuchera* hybrid**
Varietal Denomination: Peach Melba

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 11/153,514

(22) Filed: Jun. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by spring foliage color of pink to rust, creamy pink flowers on short red flowering stems, and a mounding habit.

1 Drawing Sheet

Botanical denomination: *Heuchera* hybrid.
Variety designation: 'Peach Melba'.

Cross Reference to siblings: *Heuchera* 'Lime Rickey' (U.S. Plant Pat. No. 16,210), *Heuchera* 'Marmalade' (U.S. Plant Pat. No. 15,945), *Heuchera* 'TNHEU042' (U.S. Plant patent application Ser. No. 11/083,819).

The present invention relates to a new and distinct cultivar of *Heuchera* hybrid and given the cultivar name of 'Peach Melba'. *Heuchera* is in the family Saxifragaceae. *Heuchera* 'Peach Melba' originated from a controlled cross between *Heuchera* 'Amber Waves' (U.S. Plant Pat. No. 13,348) as the seed parent and *Heuchera* 'Huntsman' (an unpatented plant) as the pollen parent. Numerous offspring were grown out from this cross. Many selections were made and trialed. Given its ornamental foliage and flower form, it is probable that *Heuchera micrantha, H. americana,* and *H. brizoides* are in its parentage.

This new *Heuchera* is distinguished by:

1. Pink to rust colored spring and summer foliage followed by greenish amber winter color;
2. Small creamy-pink flowers on dark peduncles;
3. Mounding habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old plant of *Heuchera* 'Peach Melba' growing in a one gallon container in the shade house in April in Canby, Oreg.

DETAILED PLANT DESCRIPTION

The following is a detailed description of the new *Heuchera* cultivar based on observations taken in April of a one-year-old specimen grown a one gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—15 cm tall from the top to the soil to the top of the foliage and 28 cm wide.
*Habit.*—Mounding.
*Vigor.*—Good.
*Roots.*—Fibrous, freely branching, fine, and white in color, roots develop easily from cuttings.

Leaf:

*Type.*—Simple.
*Arrangement.*—Rosette.
*Shape.*—Ovate.
*Lobing/division.*—5 to 7 shallow lobes.
*Venation.*—Palmate.
*Margins.*—Crenate.
*Apex.*—Mucronulate.
*Base.*—Cordate, lobes sometimes slightly overlapping at the base.
*Blade size.*—8 to 9.3 cm long and 7.5 to 8.3 cm wide.
*Surface texture.*—Glandular on margins and on veins on bottom side.
*Petiole description.*—6.5 to 13 cm long and 1.5 mm wide, glandular-pubescent, Greyed Purple 183C to Greyed Orange 177C.
*Leaf color.*—Spring, summer topside — Newly emerging spring leaves are Greyed Orange 166C to Greyed Orange 165C with darker veins of Greyed Orange 166B. These mature to Greyed Orange 165A to Greyed Orange 166B with a veil of between Greyed Orange 177D and White 155A. Bottom side all seasons — Grayed Purple 187C and D. Winter topside — Yellow Green 152A and 152B with amber shades of Greyed Orange 165B overlaid with a slight white veil, White 155A.

Inflorescence:

*Type.*—Thyrse.

*Number of flowers.*—70 per thyrse.

*Number of thyrse in spring.*—5.

*Peduncle.*—30 cm high and 3 mm wide, with glandular hairs, color is Greyed Purple 184A, with 2 to 3 petiolate cauline leaves (ovate to linear, blades grow to 5 cm long and 5 cm wide and are 3 lobed and crenate).

*Pedicel.*—Variable size, gladular hairs, Grayed Purple 184A.

*Bloom period.*—May in Canby, Oreg.

Flower bud:

*Size.*—2 mm wide and 5 mm long.

*Description.*—Glandular puberulent, ovoid.

*Color.*—Greyed Orange 165D overall.

Flower:

*Type.*—Perfect, zygomorphic.

*Shape.*—Campanulate.

*Size.*—6 mm long and 5 mm wide.

*Petal description.*—5 in number, extruding from the calyx, 2.5 mm long, spatulate with a clawed base, reflexed, apex acute, margin entire, White 155D on both sides, a few glandular hairs on bottom side.

*Calyx description.*—5 lobes, divided ⅓ way to the base, with glandular hairs on inside and outside, apex acute, margin entire, 5 mm long and 3 mm wide.

*Calyx color.*—Creamy pink. Red Purple 62D with Greyed Yellow 160A at the base and Greyed Orange White 164A at lobes on both sides.

*Stamen description.*—5 in number, filaments 3 mm long, White 155A, anthers are 0.5 mm long, Orange 26B, no pollen produced, male sterile.

*Pistil description.*—5 mm long, Yellow Green 154D.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERAS*

Compared to *Heuchera* 'Amber Waves' (U.S. Plant Pat. No. 13,348), the seed parent, *Heuchera* 'Peach Melba' has foliage which is less ruffled, larger, and more pink colored.

Compared to *Heuchera* 'Huntsman', the pollen parent, the new cultivar has peach colored leaves rather than green leaves with grey brown veins, and small creamy pink rather than larger salmon pink flowers.

Compared to *Heuchera* 'Marmalade' (U.S. Plant patent application Ser. No. 10/871,960), this cultivar is smaller in habit with leaves that are larger, shinier, less ruffled.

Compared to *Heuchera* 'Peach Flambé' (U.S. Plant patent application Ser. No. 11/154,434), this new variety has foliage colors that are a more muted peach shades. The new variety has a slight veil unlike *Heuchera* 'Peach Flambé'. *Heuchera* 'Peach Flambé' has white flowers rather than creamy pink flowers.

I claim:

1. A new and distinct hybrid of *Heuchera* plant as herein illustrated and described.

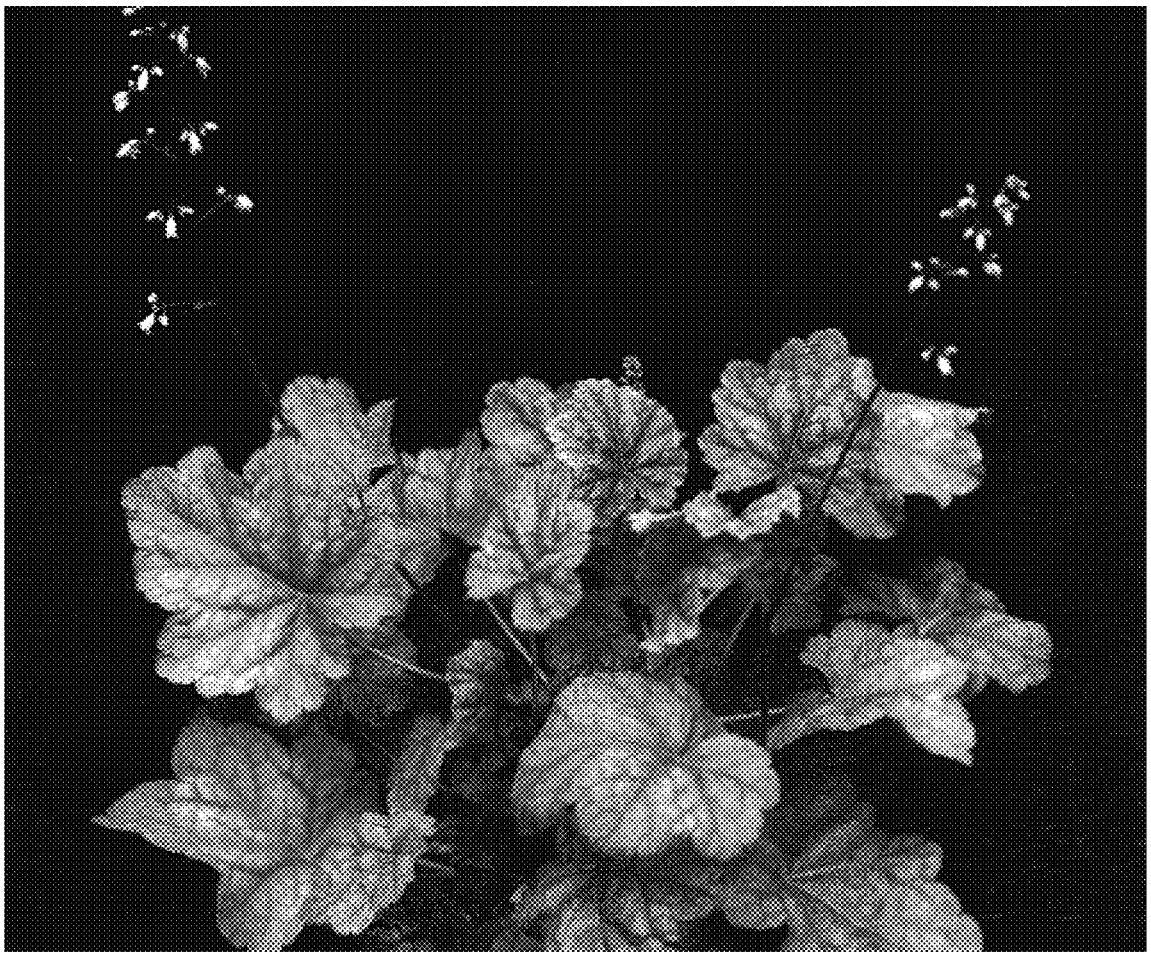

* * * * *